US006607915B1

(12) United States Patent
Monia et al.

(10) Patent No.: US 6,607,915 B1
(45) Date of Patent: Aug. 19, 2003

(54) ANTISENSE INHIBITION OF E2A-PBX1 EXPRESSION

(75) Inventors: Brett P. Monia, La Costa, CA (US); Edward Wancewicz, Poway, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/624,945

(22) Filed: Jul. 25, 2000

Related U.S. Application Data

(60) Provisional application No. 60/156,836, filed on Sep. 30, 1999.

(51) Int. Cl.⁷ .................. C07H 21/04; A61K 48/00; C12N 15/00
(52) U.S. Cl. ............... 435/375; 435/377; 536/23.1; 536/24.1; 536/24.5; 514/44
(58) Field of Search ................ 435/375, 377; 514/44; 536/23.1, 24.1, 24.5

(56) References Cited

U.S. PATENT DOCUMENTS 5,998,148 A * 12/1999 Bennett et al. ............. 435/6

FOREIGN PATENT DOCUMENTS

EP      WO 93/23057    * 5/1993

OTHER PUBLICATIONS

Harold M. Weintraub, Scientific American, Jan. 1990, pp. 40–44.*
John J. Rossi et al., Methods: A Companion to Methods in Enzymology, 5, pp. 1–5, 1993.*
Takashi Shimamoto et al., Internaitonal Journal of Hematology, 67 (1998) pp. 339–350.*
Andrea D. Branch, TIBS 23—Feb. 1998, pp. 45–50.*
Sudhir Agrawal, TIBTECH, Oct. 1996, vol. 14, pp. 376–387.*
Kuang–Yu et al., STEM Cells, 2000; 18: pp. 307–319.*
Experimental Therapeutics, Proceedings of the American Association for Cancer Research, vol. 37, Mar. 1996, pp. 421.*
Carroll, et al., "Pre–B Cell Leukemia Associated With Chromosome Translocation 1;19", *Blood,* 1984 63:3 721–724.
Crist et al., "Poor Prognosis of Children with Pre–B Acute Lymphoblastic Leukemia Is Associated With the 5 (1;19) (q23;p13): A Pediatric Oncology Group Study", *Blood* 1990 76:1 117–122.
Dedera et al., "Chimeric Homeobox Gene E2A–PBX1 Induces Proliferation, Apoptosis, and Malignant Lymphomas in Transgenic Mice", *Cell* 1993 74:833–843.
Kamps et al., "The human t(1;19) translocation in pre–B ALL produces multiple nuclear E2A–Pbx1 proteins with differing transforming potentials", *Genes & Development* 1991 5:358–368.
Kamps et al., "E2A–Pbx1, the t(1;19) Translocation Protein of Human Pre–B–Cell Acute Lymphocytic Leukemia, Causes Acute Myeloid Leukemia in Mice", *Molecular and Cellular Biology* 1993 13:1 351–357.
M.P. Kamps, "E2A–Pbx1 Induces Growth, Blocks Differentiation, and Interacts with Other Homeodomain Proteins Regulating Normal Differentiation", *Dept. Pathology, UC San Diego, School of Medicine* 25–43.
deLau, et al., "The gene encoding the granulctye colony–stimulating factor receptor is a target for deregulation in pre–B ALL by the 4(1;19)–specific oncoprotein E2A–Pbx1", *Oncogene* 1998 17:503–510.
Lengauer et al., "Genetic instabilities in human cancers", *Nature* 1998 396:643–649.

* cited by examiner

*Primary Examiner*—Sean McGarry
(74) *Attorney, Agent, or Firm*—Licata & Tyrrell P.C.

(57) ABSTRACT

Compounds, compositions and methods are provided for inhibiting E2A-Pbx1 mediated transformation. The compositions comprise antisense compounds targeted to nucleic acids encoding E2A-Pbx1. Methods of using these antisense compounds for inhibition of E2A-Pbx1 expression and for treatment of diseases, particularly cancers, associated with overexpression or constitutive activation of E2A-Pbx1 are provided.

25 Claims, No Drawings

SEQUENCE LISTING

<160> NUMBER OF SEQ ID NOS: 20

<210> SEQ ID NO 1
<211> LENGTH: 4410
<212> TYPE: DNA
<213> ORGANISM: Homo sapiens

<400> SEQUENCE: 1

```
gcctgaggtg cccgccctgg ccccaggaga atgaaccagc cgcagaggat ggcgcctgtg      60
ggcacagaca aggagctcag tgacctcctg gacttcagca tgatgttccc gctgcctgtc     120
accaacggga agggccggcc cgcctccctg gccggggcgc agttcggagg ttcaggtctt     180
gaggaccggc ccagctcagg ctcctggggc agcggcgacc agagcagctc ctcctttgac     240
cccagccgga ccttcagcga gggcacccac ttcactgagt cgcacagcag cctctcttca     300
tccacattcc tgggaccggg actcggaggc aagagcggtg agcggggcgc ctatgcctcc     360
ttcgggagag acgcaggcgt gggcggcctg actcaggctg gcttcctgtc aggcgagctg     420
gccctcaaca gccccgggcc cctgtcccct tcgggcatga aggggacctc ccagtactac     480
```

```
ccctcctact ccggcagctc ccggcggaga gcggcagacg gcagcctaga cacgcagccc    540
aagaaggtcc ggaaggtccc gccgggtctt ccatcctcgg tgtacccacc cagctcaggt    600
gaggactacg gcagggatgc caccgcctac ccgtccgcca agaccccag cagcacctat     660 cccgccccct tctacgtggc agatggcagc ctgcacccct cagccgagct ctggagtccc    720
ccgggccagg cgggcttcgg gcccatgctg gtgggggct catccccgct gcccctcccg    780
cccggtagcg gccggtggg cagcagtgga agcagcagca cgtttggtgg cctgcaccag    840
cacgagcgta tgggctacca gctgcatgga gcagaggtga acggtgggct cccatctgca    900
tcctccttct cctcagcccc cggagccacg tacggcggcg tctccagcca cacgccgcct    960
gtcagcgggg ccgacagcct cctgggctcc cgagggacca cagctggcag ctccggggat   1020
gccctcggca aagcactggc ctcgatctac tccccggatc actcaagcaa taacttctcg   1080 tccagcccctt ctaccccgt gggctccccc cagggcctgg caggaacgtc acagtggcct   1140
cgagcaggag ccccggtgc cttatcgccc agctacgacg ggggtctcca cggcctgcag   1200
agtaagatag aagaccacct ggacgaggcc atccacgtgc tccgcagcca cgccgtgggc   1260
acagccggcg acatgcacac gctgctgcct ggccacgggg cgctggcctc aggtttcacc   1320
agtcccatgt cgctgggtgg gcggcacgca ggcctggttg gaggcagcca ccccgaggac   1380
ggcctcgcag gcagcaccag cctcatgcac aaccacgcgg ccctccccag ccagccaggc   1440
accctccctg acctgtctcg gcctcccgac tcctacagtg gccagggcat ctcaccgcag   1500
cttggtcccc tctccacctc gatctacttg ctcacccagg atgacaagta ctgggcaagg   1560
cgcagaaaga caacatggc agccaagcgc tcccgcgacg cccggaggct gaaagagaac   1620
cagatcgcca tccgggcctc gttcctggag aaggagaact cggccctccg ccaggaggtg   1680
gctgacttga ggaaggagct gggcaaatgc aagaacatac ttgccaagta tgaggccagg   1740
cacgggcccc tgtaggatgg cattttgca ggctggcttt ggaatagatg gacagtttgt   1800
ttcctgtctg atagcaccac acgcaaacca acctttctga catcagcact ttaccagagg   1860
cataaacaca actgactccc attttggtgt gcatctgtgt gtgtgtgcgt gtatatgtgc   1920
ttgtgctcat gtgtgtggtc agcggtatgt gcgtgtgcgt gttcctttgc tcttgccatt   1980
ttaaggtagc cctctcatcg tcttttagtt ccaacaaaga aaggtgccat gtctttacta   2040
gactgaggag ccctctcgcg ggtctcccat cccctccctc cttcactcct gcctcctcag   2100
ctttgcttca tgttcgagct tacctactct tccaggactc tctgcttgga ttcactaaaa   2160
agggccctgg taaatagtg gatctcagtt tttaagagta caagctcttg tttctgttta   2220
gtccgtaagt taccatgcta atgaggtgca cacaataact tagcactact ccgcagctct   2280
agtcctttat aagttgcttt cctcttactt tcagttttgg tgataatcgt cttcaaatta   2340
aagtgctgtt tagatttatt agatcccata tttacttact gctatctact aagtttcctt   2400
ttaattctac caaccccaga taagtaagag tactattaat agaacacaga gtgtgttttt   2460
gcactgtctg tacctaaagc aataatccta ttgtacgcta gagcatgctg cctgagtatt   2520
actagtggac gtaggatatt ttccctacct aagaatttca ctgtcttta aaaaacaaaa   2580 agtaaagtaa tgcatttgag catggccaga ctattcccta ggacaaggaa gcagagggaa   2640
atgggaggtc taaggatgag gggttaattt atcagtacat gagccaaaaa ctgcgtcttg   2700
gattagcctt tgacattgat gtgttcggtt ttgttgttcc ccttccctca caccctgcct   2760 cgccccccact tttctagtta actttttcca tatccctctt gacattcaaa acagttactt   2820
```

-continued

| | |
|---|---|
| aagattcagt tttcccactt tttggtaata tatatatttt tgtgaattat actttgttgt | 2880 |
| ttttaaaaag aaaatcagtt gattaagtta ataagttgat gttttctaag gcccttttc | 2940 |
| ctagtggtgt cattttgaa tgcctcataa attaatgatt ctgaagctta tgtttcttat | 3000 |
| tctctgtttg cttttgaacg tatgtgctct tataaagtgg acttctgaaa atgaatgta | 3060 |
| aaagacactg tgtatctca gaggggatg gtgttgtcac aaactgtggt taatccaatc | 3120 |
| aatttaaatg tttactatag accaaaagga gagattatta aatcgtttaa tgtttataca | 3180 |
| gagtaattat aggaagttct ttttgtaca gtattttca gatataaata ctgacaatgt | 3240 |
| attttggaag acatatatta tatatagaaa agaggagagg aaaactattc catgttttaa | 3300 |
| aattatatag caaagatata tattcaccaa tgttgtacag agaagaagtg cttgggggtt | 3360 |
| tttgaagtct ttaatatttt aagccctatc actgacacat cagcatgttt tctgctttaa | 3420 |
| attaaaattt tatgacagta tcgaggcttg tgatgacgaa tcctgctcta aaatacacaa | 3480 |
| ggagctttct tgtttcttat taggcctcag aaagaagtca gttaacgtca cccaaaagca | 3540 |
| caaaatggat tttagtcaaa tatttattgg atgatacagt gttttttagg aaaagcatct | 3600 |
| gccacaaaaa tgttcacttc gaaattctga gttcctggaa tggcacgttg ctgccagtgc | 3660 |
| cccagacagt tcttttctac cctgcgggcc cgcacgtttt atgaggttga tatcggtgct | 3720 |
| atgtgtttgg tttataattt gatagatgtt tgactttaaa gatgattgtt cttttgtttc | 3780 |
| attaagttgt aaaatgtcaa gaaattctgc tgttacgaca aagaaacatt ttacgctaga | 3840 |
| ttaaaatatc ctttcatcaa tgggatttc tagtttcctg ccttcagagt atctaatcct | 3900 |
| ttaatgatct ggtggtctcc tcgtcaatcc atcagcaatg cttctctcat agtgtcatag | 3960 |
| acttgggaaa cccaaccagt aggatatttc tacaaggtgt tcattttgtc acaagctgta | 4020 |
| gataacagca agagatgggg gtgtattgga attgcaatac attgttcagg tgaataataa | 4080 |
| aatcaaaaac ttttgcaatc ttaagcagag ataaataaaa gatagcaata tgagacacag | 4140 |
| gtggacgtag agttggcctt tttacaggca aagaggcgaa ttgtagaatt gttagatggc | 4200 |
| aatagtcatt aaaaacatag aaaaatgatg tcttttaagtg gagaattgtg gaaggattgt | 4260 |
| aacatggacc atccaaattt atggccgtat caaatggtag ctgaaaaaac tatatttgag | 4320 |
| cactggtctc tcttggaatt agatgtttat atcaaatgag catctcaaat gttttctgca | 4380 |
| gaaaaaaata aaaagattct aataaaaaaa | 4410 |

<210> SEQ ID NO 2
<211> LENGTH: 2049
<212> TYPE: DNA
<213> ORGANISM: Homo sapiens

<400> SEQUENCE: 2

| | |
|---|---|
| ggctaccagc tgcatggagc agaggtgaac ggagggctcc catctgcatc ctccttctcc | 60 |
| tcagccccg gagccacgta cggcgtctcc agccacacgc cgcctgtcag cggggccgac | 120 |
| agcctcctgg gctcccgagg gaccacagct ggcagctccg gggatgccct cggcaaagca | 180 |
| ctggcctcga tctactcccc ggatcactca agcaataact tctcgtccag cccttctacc | 240 |
| cccgtgggct ccccccaggg cctggcagga acgtcacagt ggcctcgagc aggagccccc | 300 |
| ggtgccttat cgcccagcta cgacggggt ctccacggcc tgcagagtaa gatagaagac | 360 |
| cacctggacg aggccatcca cgtgctccgc agccacgccg tgggcacagc cggcgacatg | 420 |
| cacacgctgc tgcctggcca cggggcgctg gcctcaggtt tcaccggccc catgtcactg | 480 |
| ggcgggcggc acgcaggcct ggttggaggc agccaccccg aggacggcct cgcaggcagc | 540 |

-continued

```
accagcctca tgcacaacca cgcggccctc cccagccagc caggcaccct ccctgacctg      600
tctcggcctc ccgactccta cagtgttttg agtatccgag gagcccagga ggaggaaccc      660 acagacccc agctgatgcg gctggacaac atgctgttag cggaaggcgt ggcggggcct      720
gagaagggcg gagggtcggc ggcagcggcg gcagcggcgg cggcttctgg aggggcaggt      780
tcagacaact cagtggagca ttcagattac agagccaaac tctcacagat cagacaaatc      840
taccatacgg agctggagaa atacgagcag gcctgcaacg agttcaccac ccacgtgatg      900
aatctcctgc gagagcaaag ccggaccagg cccatctccc caaaggagat tgagcggatg      960
gtcagcatca tccaccgcaa gttcagctcc atccagatgc agctcaagca gagcacgtgc     1020
gaggcggtga tgatcctgcg ttcccgattt ctggatgcgc ggcggaagag acggaatttc     1080
aacaagcaag cgacagaaat cctgaatgaa tatttctatt cccatctcag caaccttac     1140 cccagtgagg aagccaaaga ggagttagcc aagaagtgtg gcatcacagt ctcccaggta     1200
tcaaactggt ttggaaataa gcgaatccgg tacaagaaga acataggtaa atttcaagag     1260
gaagccaata tttatgctgc caaaacagct gtcactgcta ccaatgtgtc agcccatgga     1320
agccaagcta actcgccctc aactcccaac tcggctggtt cttccagttc ttttaacatg     1380
tcaaactctg gagatttgtt catgagcgtg cagtcactca atggggattc ttaccaaggg     1440
gcccaggttg gagccaacgt gcaatcacag gtggataccc ttcgccatgt tatcagccag     1500
acaggaggat acagtgatgg actcgcagcc agtcagatgt acagtccgca gggcatcagt     1560
gctaatggag gttggcagga tgctactacc ccttcatcag tgacctcccc tacagaaggc     1620
cctggcagtg ttcactctga tacctccaac tgatctccca gcaatcgcat cccggctgac     1680
cctgtgcccc agttggggca ggggcaggag ggagggtttc tctcccaacg ctgaagcggt     1740
cagactggag gtcgaagcaa tcagcaaaca caataagagt ctccttctct tctcttcttt     1800
gggatgctat ttcagccaat ctggacactt ctttatactc tcttcccttt tttttctggg     1860
tagaagccac ccttccctgc ctccagctgt cagcctggtt ttcgtcatct tccctgcccc     1920
tgtgcctctg tcctagactc ccggggtccc cgccctctct catatcactg aaggatattt     1980
tcaacaattg aaggaattta aagagcaaaa aaattacaaa gaaataata aaagtgtttg     2040 tacgttttc                                                             2049
```

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 3

```
ccagggcggg cacctcaggc                                                   20
```

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 4

```
cggctggttc attctcctgg                                                   20
```

<210> SEQ ID NO 5

```
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 5
gctgggccgg tcctcaagac                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 6
ccggtcccag gaatgtggat                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 7
gactccagag ctcggctgag                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 8
ccatacgctc gtgctggtgc                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 9
tggctgcgga gcacgtggat                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 10
ctcaaaacac tgtaggagtc                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 11
```

```
cctcggatac tcaaaacact                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 12
cggatactca aaacactgta                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 13
tgggaataga aatattcatt                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 14
tttgacatgt taaaagaact                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 15 gtagggagg tcactgatga                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 16
gggatgcgat tgctgggaga                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 17
tctgaccgct tcagcgttgg                                              20

<210> SEQ ID NO 18
<211> LENGTH: 20
<212> TYPE: DNA
```

-continued

```
<213> ORGANISM: Artificial Sequence
<220> FEATURE:
<223> OTHER INFORMATION: Description of Artificial Sequence:  Synthetic

<400> SEQUENCE: 18
taaagaagtg tccagattgg                                                   20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:  Synthetic

<400> SEQUENCE: 19
accaggctga cagctggagg                                                   20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:  Synthetic

<400> SEQUENCE: 20
ccttcagtga tatgagagac                                                   20
```

US 6,607,915 B1

ANTISENSE INHIBITION OF E2A-PBX1 EXPRESSION

INTRODUCTION

This application claims the benefit of provisional U.S. Application Ser. No. 60/156,836, filed Sep. 30, 1999.

FIELD OF THE INVENTION

This invention relates to compositions and methods for modulating expression of the E2A-Pbx1 gene which results from the fusion of the E2A and Pbx1 genes. These methods can be used diagnostically or therapeutically. Furthermore, this invention is directed to treatment of conditions associated with expression of the E2A-Pbx1 gene.

BACKGROUND OF THE INVENTION

Genetic alterations are responsible for a multitude of cancers. One type of alteration is chromosomal translocation where different chromosomes are fused or where different regions within a single chromosome are fused. Both random and distinctive rearrangements can occur, with random rearrangements being common in solid tumors, while distinctive rearrangements are common in leukemias, lymphomas and sarcomas (Lengauer C., et al., *Nature,* 1998, 396, 643–649). These distinctive rearrangements involve the same breakpoints and often occur within transcription factors. The resulting transcripts can be targeted using sequence specific approaches.

Many acute leukemias are characterized by chromosomal translocations that involve transcription factors. In pediatric acute lymphoblastoid leukemia (ALL) carrying the t(1;19) chromosomal translocation, the N-terminal transactivation domain of the E2A transcription factor is fused to the homeodomain of Pbx-1 (Prl) to create the chimeric transcription factor, E2A-Pbx1 (Kamps, M. P., *Curr. Top. Microbiol. Immunol.,* 1997, 220, 25–43). This particular translocation has been found in 23% of pediatric pre-B ALL (Carroll, A., et al., *Blood,* 1984, 63, 721–724) and is associated with a poorer prognosis (Crist, W., et al., *Blood,* 1990, 76, 117–122). The resulting chimeric protein has shown transforming ability in NIH3T3 cells (Kamps, M. P., et al., *Genes Dev.,* 1991, 5, 358–368), the ability to induce malignant lymphomas in transgenic mice (Dedera, D. A., et al., *Cell,* 1993, 74, 833–843) and capable of promoting the rapid development of myeloid leukemias (Kamps, M. P. and Baltimore, D., *Mol. Cell. Biol.,* 1993, 13, 351–357).

E2A-Pbx1 physically interacts with homeodomain proteins, which are effectors of differentiation. In particular, Pbx1 interacts with Hox proteins, which are also transcription factors. Overexpression of Hox proteins can induce transformation. Pbx1 is an important contributor to differentiation, via its interaction with Hox proteins.

Expression of E2A-Pbx1 is involved in development of pre-B-cell acute lymphocytic leukemia. Expression of this protein prevents the differentiation of pre-B-cells and promotes their growth. One of the genes upregulated by E2A-Pbx-1is granulocyte colony-stimulating factor receptor (de Lau, W. B. M., et al., *Oncogene,* 1998, 17, 503–510).

Chemotherapy, including the use of methotrexate, and bone marrow transplants are the most effective treatments for leukemia and are not specific for E2A-Pbx1. There is a lack of specific inhibitors of E2A-Pbx1.

There remains a need for improved compositions and methods for inhibiting E2A-Pbx1 gene expression.

SUMMARY OF THE INVENTION

The present invention provides antisense compounds which are targeted to nucleic acids encoding E2A-Pbx1 (E2A-prl) and are capable of modulating E2A-Pbx1 mediated transformation. In one embodiment, the present invention provides oligonucleotides, including chimeric oligonucleotides, targeted to nucleic acids encoding E2A-Pbx1. The compounds of the invention are believed to be useful both diagnostically and therapeutically, and are believed to be particularly useful in the methods of the present invention.

The present invention also comprises methods of modulating E2A-Pbx1 mediated transformation, in cells and tissues, using the antisense compounds of the invention. Methods of inhibiting E2A-Pbx1 expression are provided; these methods are believed to be useful both therapeutically and diagnostically. These methods are also useful as tools, for example, for detecting and determining the role of E2A-Pbx1 in various cell functions and physiological processes and conditions and for diagnosing conditions associated with expression of E2A-Pbx1.

The present invention also comprises methods for diagnosing and treating cancers, especially pre-B-cell acute lymphocytic leukemia. These methods are believed to be useful, for example, in diagnosing E2A-Pbx1-associated disease progression. Furthermore, these methods are believed to be useful both therapeutically, including prophylactically, and as clinical research and diagnostic tools.

Thus, in a first aspect the present invention features an antisense compound having at least one modified internucleoside linkage, targeted to E2A-Pbx1 mRNA, and which inhibits the expression of the E2A-Pbx1 gene product.

In a preferred embodiment the antisense compound is an olilgonucleotide and is between 8 to 30 nucleobases in length, more preferably the antisense compound is up to 20 bases, and most preferably it is 15 to 20 bases long. In a further embodiment the modified internucleoside linkage is a phosphorothioate linkage and the nucleotide comprises a modified sugar moiety such as for example a 2'-O-methoxyethyl moiety, and/or a 5-methyl cytosine.

E2A-Pbx1 is the resulting product of the N-terminal transactivation domain of the E2A transcription factor becoming fused to the homeodomain of Pbx-1 (Prl). Thus in a preferred embodiment, the present invention features an antisense compound targeted to E2A and/or Pbx1, more preferably the antisense compound is target to bases 388–1812 of *homo sapiens* pre-B-cell leukemia transcription factor 1 (PBX1) mRNA (Genbank Accession No. NM002585) and/or bases 853–14801 of human transcription factor (E2A) mRNA (Genbank Accession number M31523). In another preferred embodiment the antisense compound is targeted to the fusion junction of E2A-Pbx1. It is also preferred that the antisense compound be contained within a pharmaceutical composition.

In an additional aspect the present invention features methods of inhibiting the expression of E2A-Pbx1 in cells or tissues. Within this method the cells or tissues are contacted with the antisense compound presently described so that expression of E2A-Pbx1 is inhibited. It is preferred that the cells or tissues are human.

In a further aspect the invention features methods for treating a human subject having a disease or condition associated with E2A-Pbx1 by administering to the subject a therapeutically or prophylactically effective amount of the antisense compound as described herein so that expression of E2A-Pbx1 is inhibited. In a preferred embodiment the disease or condition is, for example, pre-B-cell acute lymphocytic leukemia, and/or sarcomatous cancer.

DETAILED DESCRIPTION OF THE INVENTION

E2A-Pbx1 plays an important role in the development of leukemias, lymphomas and sarcomas. Expression of this gene is associated with a poor prognosis in pre-B-cell acute lymphocytic leukemia. As such, this chimeric protein represents an attractive target for treatment of such diseases. In particular, modulation of the expression of E2A-Pbx1 may be useful for the treatment of pre-B-cell acute lymphocytic leukemia.

The cDNA sequence of human E2A-Pbx1 (PRL) is available via Genbank Accession No. M31522. In accordance with Kamps et al. (supra) comparison of the sequence with the individual sequences for E2A and Pbx1 shows the fusion/junction point of the two genes to be at nucleotide 625 of Genbank Accession No. M31522. In a preferred embodiment the antisense compounds as described herein contain oligonucleotides targeted to the junction in E2A-Pbx1, such as for example oligonucleotides 154015, 15407, and 15409, SEQ ID NOS: 10, 11 and 12 respectively. Furthermore, due to the fusion of E2A to Pbx1, also included in the present invention are antisense compounds containing oligonucleotides targeted to E2A and/or Pbx1.

E2A, an Ig regulator, is normally expressed, while Pbx1 expression is thought to be only expressed embryonically. Therefore in a preferred embodiment the Pbx portion of the fusion is targeted. Since Pbx is only expressed in the fusion product, the aberrant E2A-Pbx mRNA would be reduced/ without affecting normally expressed genes. Therefore in an additional embodiment, the invention described herein provides antisense compounds targeted to Pbx1.

The present invention employs antisense compounds, particularly oligonucleotides, for use in modulating the function of nucleic acid molecules encoding E2A-Pbx1, ultimately modulating the amount of E2A-Pbx1 produced. This is accomplished by providing oligonucleotides which specifically hybridize with nucleic acids, preferably mRNA, encoding E2A-Pbx1.

This relationship between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, for example, a cellular gene (or mRNA made from the gene) whose expression is associated with a particular disease state, or a nucleic acid from an infectious agent. In the present invention, the targets are nucleic acids encoding E2A-Pbx1; in other words, a gene encoding E2A/Pbx1 fusion protein, or mRNA expressed from the E2A-Pbx1 genes. mRNA which encodes E2A-Pbx1 is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding E2A-Pbx1, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns", which are excised from a pre-mRNA transcript to yield one or more mature mRNA. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment and, in the case of in vitro assays, under conditions in which the assays are conducted.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The overall effect of interference with mRNA function is modulation of expression of E2A-Pbx1. In the context of this invention "modulation" means either inhibition or stimulation; i.e., either a decrease or increase in expression. This modulation can be measured in ways which are routine in the art, for example by Northern blot assay of mRNA expression, reverse transcriptase PCR, Western blot or ELISA assay of protein expression, or by an immunoprecipitation assay of protein expression. Effects on cell proliferation or tumor cell growth can also be measured using methods well known in the art. Inhibition is presently the preferred form of modulation.

The oligonucleotides of this invention can be used in diagnostics, therapeutics, prophylaxis, and as research reagents and in kits. Since the oligonucleotides of this invention hybridize to nucleic acids encoding E2A-Pbx1, sandwich, calorimetric and other assays can easily be constructed to exploit this fact. Provision of means for detecting hybridization of oligonucleotide with the E2A-Pbx1 genes or mRNA can routinely be accomplished. Such provision may include enzyme conjugation, radiolabelling or any other suitable detection systems. Kits for detecting the presence or absence of E2A-Pbx1 may also be prepared.

The present invention is also suitable for diagnosing genetic alterations responsible for disease states such as cancer, in particular, in patients suspected of having leukemia, such as pediatric pre-B acute lymphoblastoid leukemia. A number of assays may be formulated employing the present invention, which assays will commonly comprise contacting a tissue sample with an oligonucleotide of the invention under conditions selected to permit detection of the alterations and, usually, quantitation. In the context of this invention, to "contact" tissues or cells or cultures of tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal or a human subject.

By use of term "culture" is meant the propagation of cells. Various culture methods exist and are included within the scope of the invention, methods such as, but not limited to, tissue culture methods, batch culture methods, enrichment culture methods, and ex vivo culture methods. In all culture methods the cells to be propagated should be in a nutritive environment which allows for continued cell growth. Tissue and cell culture methods are well understood in the art as these methods have been regularly practiced in various scientific fields for years. Such cultures may be propagated in natural serum or in artificial serum as described for example in U.S. Pat. No. 4,657,866 to Kumar, Sudhir. Inasmuch as a culture represents a group of cells being observed for the presence of a genetic alteration and the determination of a cancer state such as pre-B acute lymphoblastoid leukemia, included within the scope of the invention are cultures of cells on or in a host, such as a tumor which must remain on or in the host to be propagated and treated.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

In the context of this invention, the term "olgonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The antisense compounds in accordance with this invention preferably comprise from about 5 to about 50 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkyene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'–5' linkages, 2'–5' linked analogs of these, and those having inverted polarity wherein the adjacent pairs of nucleoside units are linked 3'–5' to 5'–3' or 2'–5' to 5'–2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262. Further teaching of PNA compounds can be found in Nielsen et al. (*Science*, 1991, 254, 1497–1500).

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH$ )$_3$—CH—$_2$CH—$_2$ [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl, O-alkyl-O-alkyl, O—, S—, or N-alkenyl, or O—, S— or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH^1_2)_nOCH_3$, $O(CH_2)_2ON(CH_3)_2$, $O(CH_2)_nNH_2$, $O(CH_2)_nCH_3$, $O(CH_2)_nONH_2$, and $O(CH_2)_n ON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl; aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta* 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, and 2'-dimethylaminoethoxyethoxy (2'-DMAEOE), i.e., 2'-O—$CH_2$—O—$CH_2$—N($CH_2$)$_2$.

Other preferred modifications include 2'-methoxy (2'-O—CH$_3$), 2'-aminopropoxy (2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering* 1990, pages 858–859, Kroschwitz, J. I., ed. John Wiley & Sons, those disclosed by Englisch et al. (*Angewandte Chemie, international Edition* 1991, 30, 613–722), and those disclosed by Sanghvi, Y. S., Chapter 15, *Antisense Research and Applications* 1993, pages 289–302, Crooke, S. T. and Lebleu, B., ed., CRC Press. Certain of these nucleobases are particularly useful for increasing the binding affinity of the oligomeric compounds of the invention. These include 5-substituted pyrimidines, 6-azpyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications* 1993, CRC Press, Boca Raton, pages 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos: 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA* 1989, 86, 6553–6556), cholic acid (Manoharan et al., *Bioorg. Med. Chem. Lett.* 1994, 4, 1053–1059), a thioether, e.g., hexyl-S-tritylthiol (Manoharan et al., *Ann. N.Y. Acad. Sci.* 1992, 660, 306–309; Manoharan et al., *Bioorg. Med. Chem. Let.* 1993, 3, 2765–2770), a thiocholesterol (Oberhauser et al., *Nucl. Acids Res.* 1992, 20, 533–538), an aliphatic chain, e.g., dodecandiol or undecyl residues (Saison-Behmoaras et al., *EMBO J.* 1991, 10, 1111–1118; Kabanov et al., *FEBS Lett.* 1990, 259, 327–330; Svinarchuk et al., *Biochimie* 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.* 1995, 36, 3651–3654; Shea et al., *Nucl. Acids Res.* 1990, 18, 3777–3783), a polyamine or a polyethylene glylol chain (Manoharan et al., *Nucleosides & Nucleotides* 1995, 14, 969–973), or adamantane acetic acid (Manoharan et al., *Tetrahedron Lett.* 1995, 36, 3651–3654), a palmityl moiety (Mishra et al., *Biochim. Biophys. Acta* 1995, 1264, 229–237), or an octadecylamine or hexylamino-carbonyl-oxycholesterol moiety (Crooke et al., *J. Pharmacol. Exp. Ther.* 1996, 277, 923–937).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 5,472,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and if necessary, associated nucleic acid hybridization techniques known in the art. This RNAse H-mediated cleavage of the RNA target is distinct from the use of ribozymes to cleave nucleic acids. Ribozymes are not comprehended by the present invention.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., fluoro- or 2'-O-methoxyethyl-substituted). Chimeric oligonucleotides are not limited to those with modifications on the sugar, but may also include oligonucleosides or oligonucleotides with modified backbones, e.g., with regions of phosphorothioate (P=S). and phosphodiester (P=O) backbone linkages or with regions of MMI and P=S backbone linkages. Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa. In one embodiment, the oligonucleotides of the present invention contain a 2'-O-methoxyethyl (2'-O—$CH_2CH_2OCH_3$) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—$CH_2CH_2OCH_3$) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also preferred. Chimeric oligonucleotides comprising one or more such modifications are presently preferred.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 2'-alkoxyalkoxy derivatives, including 2'-O-methoxyethyl oligonucleotides (Martin, P., *Helv. Chim. Acta* 1995, 78, 486–504). It is also wells known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids. A pharmaceutically acceptable salts@ are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," *J. of Pharma Sci.* 1977, 66, 1–19).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; and (d) salts formed from elemental anions such as chlorine, bromine, and iodine.

The oligonucleotides of the invention may additionally or alternatively be prepared to be delivered in a Aprodrug@ form. The term Aprodrug@ indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl)phosphate] derivatives according to the methods disclosed in WO 93/24510 to Gosselin et al., published Dec. 9, 1993.

For therapeutic or prophylactic treatment, oligonucleotides are administered in accordance with this invention. Oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention may include penetration enhancers in order to enhance the alimentary delivery of the oligonucleotides. Penetration enhancers may be classified as belonging to one of five broad categories, i.e. fatty acids, bile salts, chelating agents, surfactants and non-surfactants (Lee et al., *Critical Reviews in Therapeutic Drug Carrier Systems* 1991, 8, 91–192; Muranishi, *Critical Reviews in Therapeutic Drug Carrier Systems* 1990, 7, 1–33). One or more penetration enhancers from one or more of these broad categories may be included.

Various fatty acids and their derivatives which act as penetration enhancers include, for example, oleic acid, lauric acids, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems* 1991, page 92; Muranishi, *Critical Reviews in Therapeutic Drug Carrier Systems* 1990, 7, 1; El-Hariri et al., *J. Pharm. Pharmacol.* 1992 44, 651–654).

The physiological roles of bile include the facilitation of dispersion and absorption of lipids and fat-soluble vitamins (Brunton, Chapter 38 In: Goodman & Gilman's *The Pharmacological Basis of Therapeutics,* 9th Ed., Hardman et al., eds., McGraw-Hill, New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations.

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) [Lee et al., *Critical Reviews in Therapeutic Drug Carrier Systems* 1991, page 92; Muranishi, *Critical Reviews in Therapeutic Drug Carrier Systems* 1990, 7, 1–33; Buur et al., *J. Control Rel.* 1990, 14, 43–51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems* 1991, page 92); and perfluorochemical emulsions, such as FC-43 (Takahashi et al., *J. Pharm. Phamacol.* 1988, 40, 252–257).

Non-surfactants include, for example, unsaturated cyclic ureas, 1-alkyl- and 1-alkenylazacyclo-alkanone derivatives (Lee et al., *Critical Reviews in Therapeutic Drug Carrier Systems* 1991, page 92); and non-steroidal anti-inflammatory agents such as diclofenac sodium, indomethacin and phenylbutazone (Yamashita et al., *J. Pharm. Pharmacol.* 1987, 39, 621–626).

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in at substantial reduction of the amount of nucleic acid recovered in the liver, kidney or other extracirculatory reservoirs, presumably due to competition between the carrier compound and the nucleic acid for a common receptor. In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinyl-pyrrolidone or hydroxypropyl methylcellulose, etc.); fillers (e.g., lactose and other sugars, microcrystalline cellulose, pectin, gelatin, calcium sulfate, ethyl cellulose, polacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., *Current Op. Biotech.* 1995, 6, 698–708).

The pharmaceutical compositions of the present invention may be administered in a number of ways depending upon whether local or systemic treatment is desired and upon the area to be treated. Administration may be topical (including ophthalmic, vaginal, rectal, intranasal, intradermal, epidermal, and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration. Oligonucleotides with at least one 2'-O-ethoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA) 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES). See, generally, *The Merck Manual of Diagnosis and Therapy*, 15th Ed. 1987 pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such, chemotherapeutic. agents, (e.g., 5-FU, MTX and oligonucleotide, or 5-FU, radiotherapy and oligonucleotide).

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in vitro and in in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

The following examples illustrate the present invention and are not intended to limit the same.

EXAMPLES

Example 1

Synthesis of Oligonucleotides

Unmodified oligodeoxynucleotides are synthesized on an automated DNA synthesizer (Applied Biosystems model 380B) using standard phosphoramidite chemistry with oxidation by iodine. β-cyanoethyldiisopropyl-phosphoramidites are purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step. Cytosines may be 5-methyl cytosines. (5-methyl deoxycytidine phosphoramidites available from Glen Research, Sterling, Va. or Amersham Pharmacia Biotech, Piscataway, N.J.)

2'-methoxy oligonucleotides are synthesized using 2'-methoxy β-cyanoethyldiisopropyl-phosphoramidites (Chemgenes, Needham, Mass.) and the standard cycle for unmodified oligonucleotides, except the wait step after pulse delivery of tetrazole and base is increased to 360 seconds. Other 2'-alkoxy oligonucleotides are synthesized by a modification of this method, using appropriate 2'-modified amidites such as those available from Glen Research, Inc., Sterling, Va.

2'-fluoro oligonucleotides are synthesized as described in Kawasaki et al. (*J. Med. Chem.* 1993, 36, 831–841). Briefly, the protected nucleoside $N^6$-benzoyl-2'-deoxy-2'-fluoroadenosine is synthesized utilizing commercially available 9-β-D-arabinofuranosyladenine as starting material and by modifying literature procedures whereby the 2'-α-fluoro atom is introduced by a $S_N2$-displacement of a 2'-β-O-trifyl group. Thus $N^6$-benzoyl-9-β-D-arabinofuranosyladenine is selectively protected in moderate yield as the 3',5'-ditetrahydropyranyl (THP) intermediate. Deprotection of the THP and $N^6$-benzoyl groups is accomplished using standard methodologies and standard methods are used to obtain the 5'-dimethoxytrityl-(DMT) and 5'-DMT-3'-phosphoramidite intermediates.

The synthesis of 2'-deoxy-2'-fluoroguanosine is accomplished using tetraisopropyldisiloxanyl (TPDS) protected 9-β-D-arabinofuranosylguanine as starting material, and conversion to the intermediate diisobutyryl-arabinofuranosylguanosine. Deprotection of the TPDS group is followed by protection of the hydroxyl group with THP to give diisobutyryl di-THP protected arabinofuranosylguanine. Selective O-deacylation and triflation is followed by treatment of the crude product with fluoride, then deprotection of the THP groups. Standard methodologies are used to obtain the 5'-DMT- and 5'-DMT-3'-phosphoramidites.

Synthesis of 2'-deoxy-2'-fluorouridine is accomplished by the modification of a known procedure in which 2,2'-anhydro-1-β-D-arabinofuranosyluracil is treated with 70% hydrogen fluoride-pyridine. Standard procedures are used to obtain the 5'-DMT and 5'-DMT-3'phosphoramidites.

2'-deoxy-2'-fluorocytidine is synthesized via amination of 2'-deoxy-2'-fluorouridine, followed by selective protection to give $N^4$-benzoyl-2'-deoxy-2'-fluorocytidine. Standard procedures are used to obtain the 5'-DMT and 5'-DMT-3'phosphoramidites.

2'-(2-methoxyethyl)-modified amidites were synthesized according to Martin, P. (*Helv. Chim. Acta* 1995, 78, 486–506). For lease of synthesis, the last nucleotide may be a deoxynucleotide. 2'-O—$CH_2CH_2OCH_3$ cytosines may be 5-methyl cytosines.

Synthesis of 5-Methyl Cytosine Monomers 2,2'-Anhydro[1-(β-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine 2,2'-Anhydro-5-methyluridine (195 g, 0.81 M), tris(2-methloxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine

2-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of drimethoxytrityl chloride (94.3. g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/-Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).

3'-O-Acetyl-2'-O-methoxyethyl-5'-O-dimethoxytrityl-5-methyl-4-triazoleuridine

A first solution was prepared by dissolving 3'-O-acetyl-2'-O methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting, mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N[4]-Benzoyl-2'-O-methoxyethyl-5'-O-dimethoxytrityl-5-methylcytidine

2'-O-Methoxyethyl-5'-O-dimethoxytrityl-5-methylcytidine (85g, 0.134 M) was dissolved in DMF (800 mL) and benzoic anhydride (37.2 g, 0.165 M) was added with stirring. After stirring for 3 hours, tic showed the reaction to be approximately 95% complete. The solvent was evaporated and the residue azeotroped with MeOH (200 mL). The residue was dissolved in $CHCl_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N$^4$-Benzoyl-2'-O-methoxyethyl-5'-O-dimethoxytrityl-5-methylcytidine-3'-amidite N$^4$-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc\Hexane (3:1) as the eluting solvent. The pure fractions were combined to give 90.6 g (87%) of the title compound.

5-methyl-2'-deoxycytidine (5-me-C) containing oligonucleotides were synthesized according to published methods (Sanghvi et al., *Nucl. Acids Res.* 1993, 21, 3197–3203) using commercially available phosphoramidites (Glen Research, Sterling Va. or ChemGenes, Needham Mass.).

2'-(Dimethylaminooxyethyl) Nucleoside Amidites

2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O$^2$-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5l-O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%); contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over P$_2$O$_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819, 86%).

5'-O-tert-butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.1 g, 4.5 mmol) was dissolved in dry CH$_2$Cl$_2$ (4.5 mL) and methylhydrazine (300 mL, 4.64 mmol) was added dropwise at −10° C. to 0° C. After 1 hr the mixture was filtered, the filtrate was washed with ice cold CH$_2$Cl$_2$ and the combined organic phase was washed with water, brine and dried over anhydrous Na$_2$SO$_4$. The solution was concentrated to get 2'-O-(aminooxyethyl)thymidine, which was then dissolved in MeOH (67.5 mL). To this formaldehyde (20% aqueous solution, w/w, 1.1 eg.) was added and the mixture for 1 hr. Solvent was removed under vacuum; residue chromatographed to get 5'-O-tert-butyldiphenylsilyl-2'-O-[(2-formadoximinooxy)ethyl]-5-methyluridine as white foam (1.95, 78%).

5'-O-tert-Butyldiphenylsilyl-2'-O-[N,N-dimethylaminooxyethyl]-5-methyluridine 5'-O-tert-butyldiphenylsilyl-2'-O-[(2-formadoximinooxy)ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10 ° C. After that the reaction vessel was removed from the ice bath and stirred at room temperature for 2 hr, the reaction monitored by TLC (5% MeOH in CH$_2$Cl$_2$). Aqueous NaHCO$_3$ solution (5%, 10 mL) was added and extracted with ethyl acetate (2×20mL). Ethyl acetate phase was dried over anhydrous Na$_2$SO$_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added; and reaction mixture stirred at 10° C. for 10 minutes. After 10 minutes, the reaction mixture was removed from the ice bath and stirred at room temperature for 2 hrs. To the reaction mixture 5% NaHCO$_3$ (25 mL) solution was added and extracted with ethyl acetate (2×25 mL). Ethyl acetate layer was dried over anhydrous Na$_2$SO$_4$ and evaporated to dryness. The residue obtained was purified by flash column chromatography and eluted with 5% MeOH in CH$_2$Cl$_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in CH$_2$Cl$_2$). Solvent was removed under vacuum and the residue placed on a flash column and eluted with 10% MeOH in CH$_2$O$_2$ to get 2'-O-(dimethylaminooxyethyl)-5-methyluridine (766mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over P$_2$O$_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in CH$_2$Cl$_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over P$_2$O$_5$ under high vacuum overnight at 40° C. Then the reaction mixture was dissolved in anhydrous acetonitrile (8.4 mL) and 2-cyanoethyl-N,N,N$^1$-N-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous NaHCO$_3$ (40 mL) Ethyl acetate layer was dried over anhydrous Na$_2$SO$_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

Oligonucleotides having methylene(methylimino) (MMI) backbones are synthesized according to U.S. Pat. No. 5,378,825, which is coassigned to the assignee of the present invention and is incorporated herein in its entirety. For ease of synthesis, various nucleoside dimers containing MMI linkages are Synthesized and incorporated into oligonucleotides. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al. (*Acc. Chem. Res.* 1995, 28, 366–374). The amide moiety is readily accessible by simple and well-known synthetic methods and is compatible with the conditions required for solid phase synthesis of oligonucleotides.

Oligonucleotides with morpholino backbones are synthesized according to U.S. Pat. 5,034,506 (Summerton and Weller).

Peptide-nucleic acid (PNA) oligomers are synthesized according to P. E. Nielsen et al. (*Science* 1991, 254, 1497–1500)

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels or capillary gel electrophoresis and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al. (*J. Biol. Chem.* 1991, 266, 18162). Results obtained with HPLC-purified material were similar to those obtained with non-HPLC purified material.

Alternatively, oligonucleotides are synthesized in 96 well plate format via solid phase P(III) phosphoramidite chemistry on an automated synthesizer capable of assembling 96 sequences simultaneously in a standard 96 well format. Phosphodiester internucleotide linkages are afforded by oxidation with aqueous iodine. Phosphorothioate internucleotide linkages are generated by sulfurization utilizing 3,H-1,2 benzodithiole-3-one 1,1 dioxide (Beaucage Reagent) in anhydrous acetonitrile. Standard base-protected beta-cyanoethyl-di-isopropyl phosphoramidites are purchased from commercial vendors (e.g. PE-Applied Biosystems, Foster City, Calif., or Pharmacia, Piscataway, N.J.). Non-standard nucleosides are synthesized as per published methods. They are utilized as base protected beta-cyanoethyldiisopropyl phosphoramidites.

Oligonucleotides are cleaved from support and deprotected with concentrated $NH_4OH$ at elevated temperature (55–60° C.) for 12–16 hours and the released product then dried in vacuo. The dried product is then re-suspended in sterile water to afford a master plate from which all analytical and test plate samples are then diluted utilizing robotic pipettors.

2. The cDNA sequence of human E2A-Pbx1 (PRL) is available via Genbank Accession No. M31522. As described above a comparison of the sequence with the individual sequences for E2A and Pbx1 provides evidence that the fusion/junction point of the two genes is located at nucleotide 625 of Genbank Accession No. M31522. Antisense compounds were targeted to the junction in E2A-Pbx1, for example oligonucleotides 15405, 15407, and 15409, SEQ ID NOS: 10, 11 and 12 respectively. Furthermore, due to the fusion of E2A to Pbx1, antisense compounds containing oligonucleotides targeted to E2A and/or Pbx1 were also designed. Oligonucleotides were synthesized as chimeric oligonucleotides ("gapmers"), 20 nucleotides in length, composed of a central "gap" region consisting of eight 2'-deoxynucleotides, which is flanked on both sides (5' and 3' directions) by six-nucleotide "wings." The wings are composed of 2'-methoxyethyl (2'-MOE) nucleotides. The internucleoside (backbone) linkages are phosphorothioate (P=S) throughout the oligonucleotide. All 2'-MOE cytosines were 5-methyl-cytosines. These oligonucleotide sequences are shown in Table 1.

TABLE 1

Nucleotide Sequences of Human E2A-Pbx1 Chimeric (deoxy gapped) Phosphorothioate Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 16107 | CCAGGGCGGGCACCTCAGGC | 3 | 0001–0020[a] | 5'-UTR |
| 16108 | CGGCTGGTTCATTCTCCTGG | 4 | 0023–0042[a] | start |
| 16109 | GCTGGGCCGGTCCTCAAGAC | 5 | 0176–0195[a] | coding |
| 16110 | CCGGTCCCAGGAATGTGGAT | 6 | 0300–0319[a] | coding |
| 16111 | GACTCCAGAGCTCGGCTGAG | 7 | 0699–0718[a] | coding |
| 16112 | CCATACGCTCGTGCTGGTGC | 8 | 0834–0853[a] | coding |
| 16113 | TGGCTGCGGAGCACGTGGAT | 9 | 0376–0395[b] | coding |
| 16114 | CTCAAAACACTGTAGGAGTC | 10 | 0613–0632[b] | coding |
| 16115 | CCTCGGATACTCAAAACACT | 11 | 0622–0641[b] | coding |
| 16116 | CGGATACTCAAAACACTGTA | 12 | 0619–0638[b] | coding |
| 16117 | TGGGAATAGAAATATTCATT | 13 | 1105–1124[b] | coding |
| 16118 | TTTGACATGTTAAAAGAACT | 14 | 1366–1385[b] | coding |
| 16119 | GTAGGGGAGGTCACTGATGA | 15 | 1594–1613[b] | coding |
| 16120 | GGGATGCGATTGCTGGGAGA | 16 | 1654–1673[b] | 3'-UTR |
| 16121 | TCTGACCGCTTCAGCGTTGG | 17 | 1725–1744[b] | 3'-UTR |
| 16122 | TAAAGAAGTGTCCAGATTGG | 18 | 1816–1835[b] | 3'-UTR |
| 16123 | ACCAGGCTGACAGCTGGAGG | 19 | 1880–1899[b] | 3'-UTR |
| 16124 | CCTTCAGTGATATGAGAGAC | 20 | 1955–1974[b] | 3'-UTR |

[1]Emboldened residues are 2'-methoxyethoxy residues, 2'-methoxyethoxy cytosine residues are 5-methyl-cytosines; all linkages are phosphorothioate linkages.
[2] [a]Coordinates from Genbank Accession No. M95586, locus name "HUME2AHLF", SEQ ID NO. 1;
[b]Coordinates from Genbank Accession No. M31522, locus name "HUMTRAA1", SEQ ID NO. 2.

Example 2

Human E2A-Pbx1 Obigonucleotide Sequences

Antisense oligonucleotides were designed to target human E2A-Pbx1. Target sequence data for E2A are from the E2A portion of human E2A-HLA fusion protein (E2A-HLF) mRNA sequence published by Inaba, T., et al. (*Science*, 1992, 257, 531–534); Genbank Accession No. M95586, provided herein as SEQ ID NO: 1, or for E2A-Pbx1 (PRL)targets the Human translocation (t1;19) fusion protein (E2A-PRL) mRNA, 3' end sequence published by Kamps, M. P., et al. (Cell, 1990, 60, 547–555); Genbank accession number M31522, provided herein as SEQ ID NO:

Example 3

Antisense Inhibition of E2A-Pbx1

Human Leukemia pre-B-cells (697 cell line) were drawn up and expelled from a pipette several times to produce a homogeneous single cell suspension (this step is repeated twice). 10 ul were counted on the hemocytometer while the remaining cell suspension was centrifuged (1000 rpm, 5', 15° C.).

The final cell pellet was resuspended in complete media. Eppendorf (1.5 ml) tubes were pre-aliquoted with the desired oligonucleotide in 40 ul. Cell suspension (360 ul)

was combined with oligo and transfected with oligonucleotide by elecotroporation (225V, 1000 μF, 13 ohm) using a BTX Electro Cells Manipulator 600 (Biotechnologies and Experimental Research, Inc. (BTX), San Diego Calif.). Oligonucleotide concentration was 10 μM. Post-electroporation but prior to plating the cells were added to 15 ml conical centrifuge tubes with 10 ml of complete media supplemented with Penicillin/Streptomycin sulfate (10 U/ml/10 ug/ml). The cell/oligo mix was electroporated then poured into 10 cm tissue culture dishes and incubated for a selected period at 37° C., 5% $CO_2$ prior to harvest.

RNA was isolated by GITC/CsCl isolation and 5 μg of RNA was electrophoresed for Northern blot analysis. RNA levels were normalized to G3PDH levels. An 8.0 kb E2A-Pbx1 transcript was detected and quantitated. Results are shown in Table 2.

TABLE 2

Antisense inhibition of E2A-Pbx1

| ISIS No: | SEQ ID NO: | GENE TARGET REGION | % mRNA EXPRESSION | % mRNA INHIBITION |
|---|---|---|---|---|
| 16107 | 3 | 5'-UTR | 73 | 27 |
| 16108 | 4 | start | 54 | 46 |
| 16109 | 5 | coding | 77 | 23 |
| 16110 | 6 | coding | 87 | 13 |
| 16111 | 7 | coding | 65 | 35 |
| 16112 | 8 | coding | 46 | 54 |
| 16113 | 9 | coding | 61 | 39 |
| 16114 | 10 | coding | 63 | 37 |
| 16115 | 11 | coding | 68 | 32 |
| 16116 | 12 | coding | 39 | 61 |
| 16117 | 13 | coding | 46 | 54 |
| 16118 | 14 | coding | 87 | 13 |
| 16119 | 15 | coding | 69 | 31 |
| 16120 | 16 | 3'-UTR | 65 | 35 |

TABLE 2-continued

Antisense inhibition of E2A-Pbx1

| ISIS No: | SEQ ID NO: | GENE TARGET REGION | % mRNA EXPRESSION | % mRNA INHIBITION |
|---|---|---|---|---|
| 16121 | 17 | 3'-UTR | 43 | 57 |
| 16122 | 18 | 3'-UTR | 63 | 37 |
| 16123 | 19 | 3'-UTR | 26 | 74 |
| 16124 | 20 | 3'-UTR | 29 | 71 |

In the above experiment, ISIS 16108, 16112, 16121, 16123 and 16124 (SEQ ID NO: 4, 8, 17, 19 and 20) gave at least 45% inhibition of E2A-Pbx1 mRNA levels.

Example 4

Dose Response of Antisense Oligonucleotides Targeted to E2A-Pbx-1

Dose response measurements were performed using ISIS 16108, 16112, 16121, 16123 and 16124 (SEQ ID NOS: 4, 8, 17, 19 and 20). Cells were electroporated as described above at oligonucleotide concentrations of 1, 5, 10 and 20 μM. Results were normalized to G3PDH levels and an $IC_{50}$ was calculated; this is the concentration of oligonucleotide which gives 50% inhibition of target mRNA levels. Results are shown in Table 3. No $IC_{50}$ is shown for ISIS 16108, which gave a maximum inhibition of 35% at the concentrations tested.

TABLE 3

Dose response antisense inhibition of E2A-Pbx1 mRNA levels

| ISIS # | SEQ ID NO: | $IC_{50}$ (in μM) |
|---|---|---|
| 16108 | 4 | — |
| 16112 | 8 | 8.9 |
| 16121 | 17 | 9.2 |
| 16123 | 19 | 3.7 |
| 16124 | 20 | 7 |

What is claimed is:

1. An antisense compound 8 to 30 nucleobases in length targeted to nucleobases 1 through 20 of a 5' untranslated region, nucleobases 23 through 42 of a start codon region, nucleobases 176–195, or nucleobases 699 through 718 of a nucleic acid molecule encoding E2 A-Pbx1 of SEQ ID NO: 1, or nucleobases 376 through 395, nucleobases 1105 through 1124, or nucleobases 1594 through 1613 of a coding region, or nucleobases 1725 through 1744, nucleobases 1816 through 1835, or nucleobases 1955 through 1974 of a 3'-untranslated region of a nucleic acid encoding E2A-Pbx1 of SEQ ID NO: 2, wherein said antisense compound specifically hybridizes with one of said regions and inhibits the expression of E2A-Pbx1.

2. The antisense compound of claim 1 which is an antisense oligonucleotide.

3. An antisense compound up to 30 nucleobases in length comprising at least an 8-nucleobase portion of SEQ ID NO: 3, 4, 5, 7, 9, 10, 13, 15, 17, 18 or 20 which inhibits the expression of E2A-Pbx1.

4. The antisense compound of claim 2 wherein the antisense oligonucleotide comprises at least one modified internucleoside linkage.

5. The antisense compound of claim 4 wherein the modified internucleoside linkage is a phosphorothioate linkage.

6. The antisense compound of claim 2 wherein the antisense oligonucleotide comprises at least one modified sugar moiety.

7. The antisense compound of claim 6 wherein the modified sugar moiety is a 2'-O-methoxyethyl moiety.

8. The antisense compound of claim 2 wherein the antisense oligonucleotide comprises at least one modified nucleobase.

9. The antisense compound of claim 8 wherein the modified nucleobase is a 5-methyl cytosine.

10. The antisense compound of claim 2 wherein the antisense oligonucleotide is a chimeric oligonucleotide.

11. A composition comprising the antisense compound of claim 1 and a pharmaceutically acceptable carrier or diluent.

12. The composition of claim 11 further comprising a colloidal dispersion system.

13. A method of inhibiting the expression of E2A-Pbx1 in cells or tissues comprising contacting said cells or tissues in vitro with the antisense compound of claim 1 so that expression of E2A-Pbx1 is inhibited.

14. The antisense compound of claim 3 which is an antisense oligonucleotide.

15. The antisense compound of claim 14 wherein the antisense oligonucleotide comprises at least one modified internucleoside linkage.

16. The antisense compound of claim 15 wherein the modified internucleoside linkage is a phosphorothioate linkage.

17. The antisense compound of claim 14 wherein the antisense oligonucleotide comprises at least one modified sugar moiety.

18. The antisense compound of claim 17 wherein the modified sugar moiety is a 2'-O-methoxyethyl sugar moiety.

19. The antisense compound of claim 14 wherein the antisense oligonucleotide comprises at least one modified nucleobase.

20. The antisense compound of claim 19 wherein the modified nucleobase is a 5-methylcytosine.

21. The antisense compound of claim 14 wherein the antisense oligonucleotide is a chimeric oligonucleotide.

22. A method of inhibiting the expression of E2A-Pbx1 in human cells or tissues comprising contacting said cells or tissues in vitro with the antisense compound of claim 3 so that expression of E2A-Pbx1 is inhibited.

23. A composition comprising the antisense compound of claim 3 and a pharmaceutically acceptable carrier or diluent.

24. The composition of claim 23 further comprising a colloidal dispersion system.

25. The composition of claim 23 wherein the antisense compound is an antisense oligonucleotide.

* * * * *

UNITED STATES PATENT AND TRADEMARK OFFICE
CERTIFICATE OF CORRECTION

PATENT NO. : 6,607,915 B1
DATED : August 19, 2003
INVENTOR(S) : Brett P. Monia et al.

It is certified that error appears in the above-identified patent and that said Letters Patent is hereby corrected as shown below:

Title page,
Item [56], References Cited, OTHER PUBLICATIONS, "Takashi et al." reference, delete "Internaitonal" and insert therefor -- International --; and "Kuang-Yu et al." reference, please insert -- Jen -- after "Kuang-Yu".

Signed and Sealed this

Eighteenth Day of May, 2004

JON W. DUDAS
*Acting Director of the United States Patent and Trademark Office*